United States Patent
Ninomiya et al.

(10) Patent No.: US 8,913,712 B2
(45) Date of Patent: Dec. 16, 2014

(54) X-RAY CT APPARATUS

(75) Inventors: Hiroaki Ninomiya, Tokyo (JP);
Takayuki Kadomura, Tokyo (JP);
Hideki Imaizumi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 415 days.

(21) Appl. No.: 13/406,717

(22) Filed: Feb. 28, 2012

(65) Prior Publication Data
US 2012/0243655 A1 Sep. 27, 2012

(30) Foreign Application Priority Data

Mar. 23, 2011 (JP) ................. 2011-064071

(51) Int. Cl.
| | |
|---|---|
| *A61B 6/04* | (2006.01) |
| *H05G 1/20* | (2006.01) |
| *H05G 1/60* | (2006.01) |
| *G01N 23/083* | (2006.01) |
| *A61B 6/02* | (2006.01) |
| *A61B 6/03* | (2006.01) |
| *A61B 6/00* | (2006.01) |

(52) U.S. Cl.
CPC ............... *A61B 6/0457* (2013.01); *A61B 6/027* (2013.01); *A61B 6/032* (2013.01); *A61B 6/4035* (2013.01); *A61B 6/488* (2013.01); *A61B 6/542* (2013.01); *A61B 6/545* (2013.01); *A61B 6/547* (2013.01); *Y10S 378/901* (2013.01)

USPC ................ 378/20; 378/95; 378/209; 378/901

(58) Field of Classification Search
USPC ......... 378/4–20, 91, 95, 98, 98.5, 98.12, 162, 378/163, 165, 204, 205, 208–210, 901
See application file for complete search history.

(56) References Cited

U.S. PATENT DOCUMENTS

| | | | |
|---|---|---|---|
| 4,649,555 A * | 3/1987 | Matsubayashi | 378/4 |
| 2010/0232566 A1* | 9/2010 | Hirokawa et al. | 378/5 |

FOREIGN PATENT DOCUMENTS

| | | |
|---|---|---|
| JP | 2007-267783 | 10/2007 |
| JP | 2010-57731 | 3/2010 |
| JP | 2010-187812 | 9/2010 |

* cited by examiner

*Primary Examiner* — Anastasia Midkiff
(74) *Attorney, Agent, or Firm* — Cooper Dunham LLP

(57) ABSTRACT

There is provided an X-ray CT apparatus that allows easy and correct confirmation of which position a bed can be moved to and which region can be imaged. The X-ray CT apparatus performs imaging for obtaining a scanogram 301 (S101), displays the scanogram 301 (S102), and calculates a transversely movable region 304 (S103). Further, the X-ray CT apparatus inputs size of a bow tie filter 103 (S201), inputs a transverse movement destination of a bed 106 (S105), calculates an imageable region on the basis of the size of the bow tie filter and the transverse movement destination 302 (S202), and displays the imageable region 305 (S203).

13 Claims, 13 Drawing Sheets

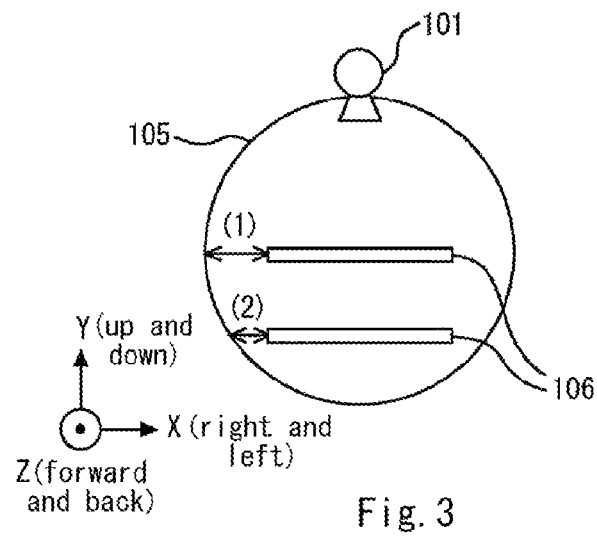
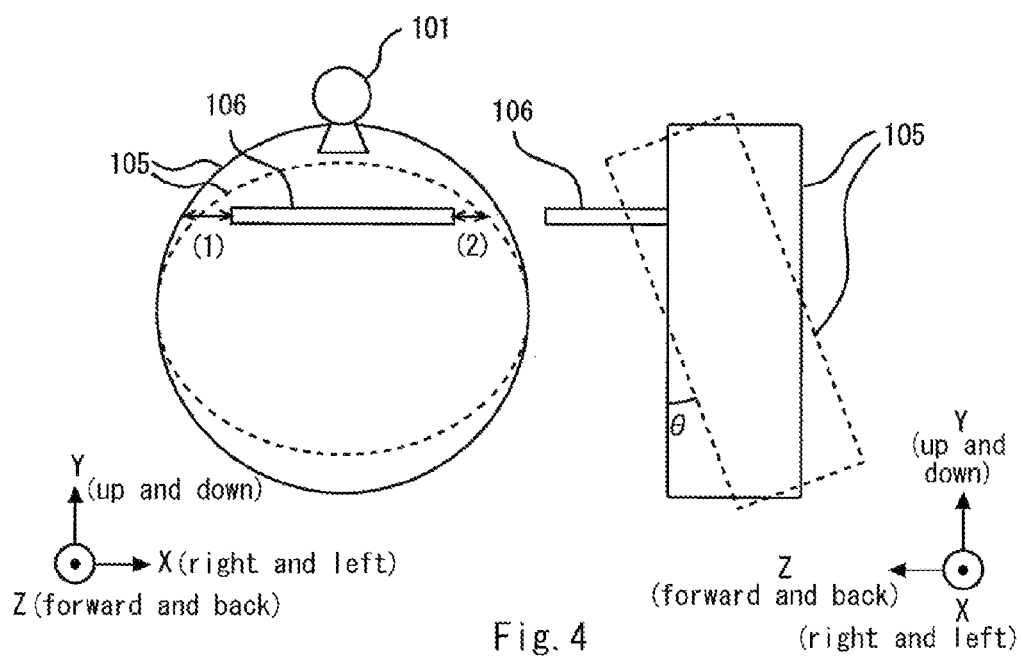

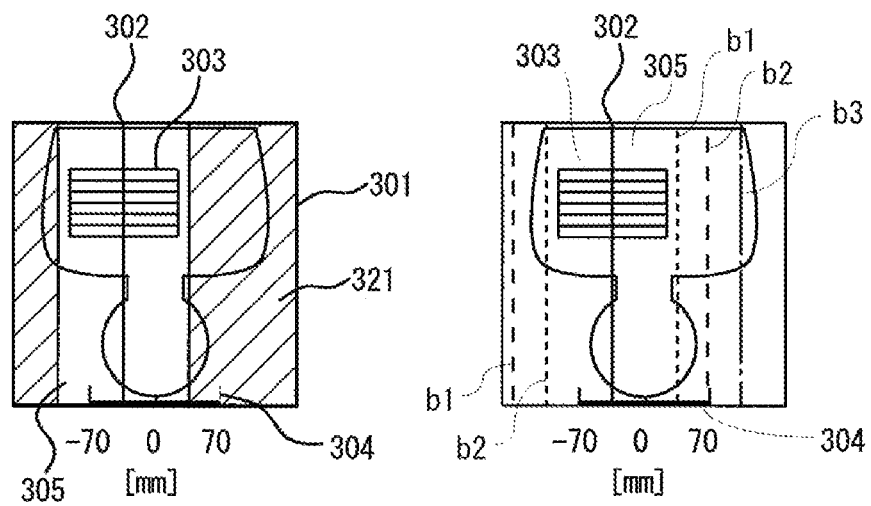
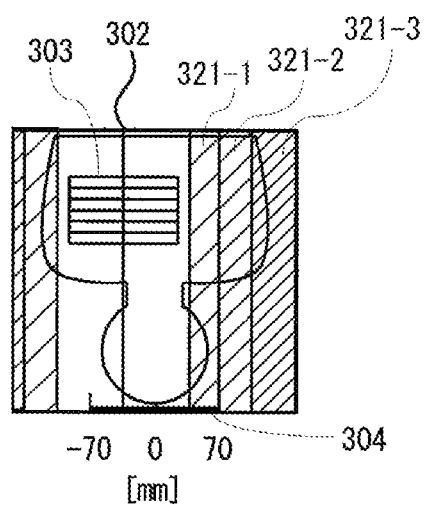
Fig. 9

X-RAY CT APPARATUS

TECHNICAL FIELD

The present invention relates to an X-ray CT (computed tomography) apparatus, in which a bed for placing a subject is movable along the transverse direction (body width direction).

BACKGROUND ART

Conventional X-ray CT apparatuses have a function of specifying a position to which a bed is moved along the body axis direction on a reference image (scanogram, scanning image etc.) displayed on a display. The scanogram is an image obtained for determining a position of a subject at the time of main imaging, and the scanning image is a CT image obtained in the main imaging.

In recent years, there is proposed a method of moving a bed for placing a subject along the transverse direction (body width direction) or the height direction (body thickness direction), in addition to the body axis direction. If a site to be imaged is placed at the revolution center of the gantry by moving the bed along the transverse direction or height direction, improvement of spatial resolution of CT images can be expected.

Patent document 1: Japanese Patent Unexamined Publication No. 2007-267783
Patent document 2: Japanese Patent Unexamined Publication No. 2010-57731
Patent document 3: Japanese Patent Unexamined Publication No. 2010-187812

For example, Patent document 1 proposes a mechanism for setting an imaging region at an objective site on a scanogram, and moving a bed to the center position of the region. In the mechanism described in Patent document 1, a bow tie filter is automatically set in order to reduce dose of regions other than the imaging region. However, in Patent document 1, whether the bed can be safely moved, that is, whether the subject may not contact with a gantry when the bed is moved, is not taken into consideration.

Therefore, Patent document 2 proposes a mechanism for setting a movement destination by using a marker, and proposes a setting using not only a scanogram, but also a scanning image, as the reference image.

Moreover, Patent document 3 proposes a mechanism for providing guide display of a region in which a bed can be safely moved.

PRIOR ART REFERENCES

Patent documents

SUMMARY OF THE INVENTION

Object to be Achieved by the Invention

However, since the bed can move only in the range of the diameter of the opening of the gantry, the movable regions of the bed for the transverse direction and the height direction are limited. In the mechanism of Patent document 2, after a movement destination is inputted, it is judged whether the bed can move to that position. Therefore, if the bed cannot move to the inputted destination, it is necessary to input a destination again, or obtain a reference image again. Moreover, since size of the imageable region is limited by the set bow tie filter, and the position of the imageable region changes depending on the position to which the bed is moved. In the mechanism of Patent document 2, after a region to be imaged is inputted, it is judged whether the region can be imaged or not. Therefore, if the inputted region cannot be imaged, it is necessary to input a region again, or obtain a reference image again, after the judgment.

In the mechanism of Patent document 3, a region in which a bed can safely move is displayed as a guide, and therefore such a situation that the bed cannot be moved to the inputted position can be avoided to some extent. However, the mechanism of Patent document 3 does not calculate the movable region or the imageable region with taking the filter size of the bow tie filter for adjusting the radiation intensity of X-rays, gantry tilt angle, and so forth into consideration. Therefore, with the mechanism of Patent document 3, if the filter size of the bow tie filter, gantry tilt angle, and so forth are different from those as usual imaging conditions, to which position the bed can be moved, or which region can be imaged cannot necessarily be displayed correctly.

Therefore, an object of the present invention is to provide an X-ray CT apparatus that allows easy and correct confirmation of position to which the bed can be moved and region that can be imaged regardless of the imaging conditions.

Means for Achieving the Object

In order to achieve the aforementioned object, according to the present invention, in an X-ray CT apparatus, a movable region calculating unit that calculates a movable region of a bed on the basis of positional information of the bed and size of a subject is provided, and at the same time, a movement destination setting unit that sets a position to which the bed is moved in the movable region calculated by the movable region calculating unit is also provided. In calculation of the movable region, the movable region calculating unit uses positional information of the bed for the transverse direction for the movable region of the bed for the up and down direction, and height (positional information for the up and down direction) of the bed for the movable region of the bed for the transverse direction. The movable region calculating unit also takes the gantry tilt angle into consideration in calculation of the movable regions. The X-ray CT apparatus of the present invention comprises a displaying unit that displays movable regions and set movement destination together with a reference image obtained by the X-ray CT apparatus.

According to the present invention, in the X-ray CT apparatus, a unit that calculates an imageable region on the basis of a movement destination of the bed set by the movement destination setting unit and size of a filter for adjusting radiation intensity of X-rays is also provided. The displaying unit displays the imageable region calculated by the imageable region calculating unit together with a reference image.

An embodiment of the present invention is an X-ray CT apparatus comprising a reference image acquisition unit that collects a reference image by irradiating a subject placed on a bed with X-rays, a movable region calculating unit that calculates a transversely movable region of the bed on the basis of height of the bed and size of the subject, and/or calculates an up and down movable region of the bed on the basis of position of the bed for the transverse direction and size of the subject, a movement destination setting unit that sets a movement destination of the bed in the transversely movable region and/or the up and down movable region calculated by the movable region calculating unit, a filter size setting unit that sets size of a filter for adjusting radiation intensity of the X-rays, an imageable region calculating unit that calculates an imageable region on the basis of the movement destination of the bed set by the movement destination setting unit and the filter size set by the filter size setting unit, and a displaying unit that displays the imageable region calculated by the imageable region calculating unit superimposed on the reference image.

Another embodiment of the present invention is an X-ray CT apparatus comprising a gantry that has an opening and can be tilted with respect to the vertical direction, and a bed that can move in the opening of the gantry, which is provided with a reference image acquisition unit that collects a reference image by irradiating a subject placed on a bed with X-rays, a movable region calculating unit that calculates a movable region of the bed on the basis of positional information of the bed, tilt angle of the gantry, and size of the subject, a movement destination setting unit that sets a movement destination of the bed within the movable region calculated by the movable region calculating unit, and a displaying unit that displays the movable region of the bed and/or the movement destination of the bed set by the movement destination setting unit together with the reference image.

Effect of the Invention

According to the present invention, movable region of the bed can be easily and correctly confirmed by visual inspection. Therefore, whether an objective site of imaging can be moved to the revolution center can be easily judged. Moreover, an imageable region can be easily and correctly confirmed by visual inspection after the bed is moved. Therefore, whether position of a subject or setting of movement of the bed is problematic or not can be easily judged.

BRIEF DESCRIPTION OF THE DRAWINGS

FIG. 3 shows transversely movable distance of the bed (1) for the case where height of the bed is equal to the height of the center of the opening, and transversely movable distance of the bed (2) for the case where height of the bed is lower than that mentioned above.

FIG. 4 shows transversely movable distance of the bed (1) for the case where the gantry is not tilted, and transversely movable distance of the bed (2) for the case where the gantry is tilted.

FIG. 9 shows examples of display of imageable region, where various imageable regions corresponding to bow tie filter sizes are displayed.

BEST MODES FOR CARRYING OUT THE INVENTION

Hereafter, embodiments of the present invention will be explained in detail with reference to the drawings.

First, whole configuration of an X-ray CT apparatus 1 will be explained, which is common to all the embodiments described below.

Figure 1:
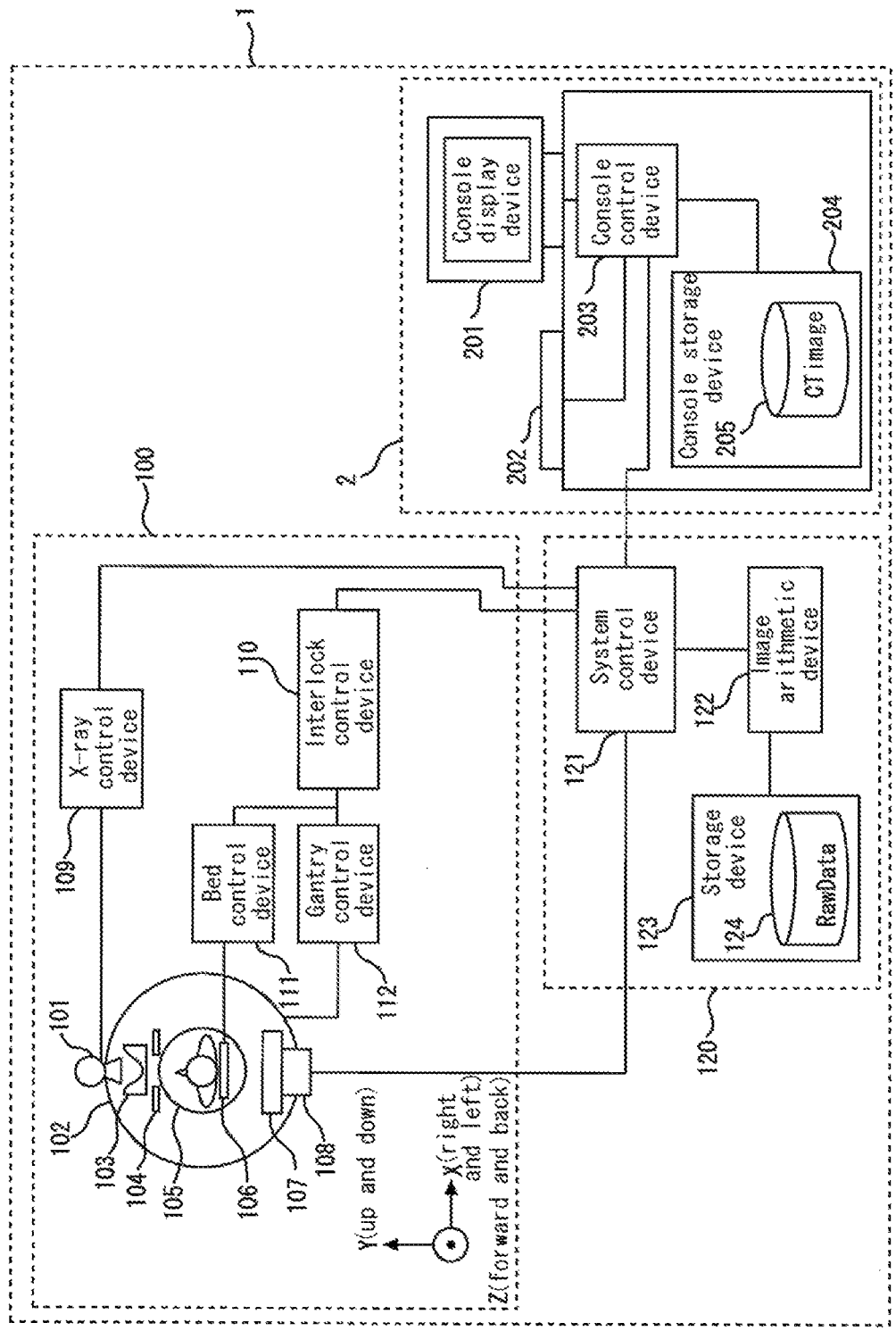
FIG. 1 shows a whole configuration of an X-ray CT apparatus.

As shown in FIG. 1, the X-ray CT apparatus 1 comprises a scanning gantry part 100, a system control part 120, and a console 2.

The scanning gantry part 100 comprises an X-ray tube 101, a gantry (revolving disk) 102, a bow tie filter 103, a collimator 104, an opening 105, a bed 106, an X-ray detector 107, a data acquisition device 108, an X-ray control device 109, an interlock control device 110, a bed control device 111, and a gantry control device 112.

The X-ray tube 101 is a device for irradiating a subject placed on the bed 106 with X-rays.

The bow tie filter 103 is a device for decreasing radiation intensity of the X-rays radiated from the X-ray tube 101.

The collimator 104 is a device for restricting irradiation range of the X-rays radiated from the X-ray tube 101.

The gantry 102 has the opening 105, into which the subject placed on the bed 106 is inserted, carries the X-ray tube 101 and the X-ray detector 107, and rotates around the subject.

The X-ray detector 107 is disposed so as to oppose the X-ray tube 101, and is a device for measuring spatial distribution of transmitted X-rays by detecting X-rays penetrating the subject, which comprises many X-ray detectors disposed along the revolution direction of the gantry 102, or two-dimensionally disposed along the revolution direction and the revolution axis direction of the gantry 102.

The data acquisition device 108 is a device for collecting X-ray doses detected by the X-ray detector 107 as digital data.

The X-ray control device 109 is a device for controlling electric power (tube current and tube voltage) applied to the X-ray tube 101.

The bed 106 is constituted with a top on which a subject is placed, and a support that supports the top.

The top is supported by the support so that it can move up and down, backward and forward, and right and left. In the following descriptions, movement of the bed 106 means a movement of the top on which a subject is placed.

The bed control device 111 is a device for controlling up and down, backward and forward, and right and left movements of the bed 106. In this specification, the up and down direction Y of the bed refers to the vertical direction with respect to the bed 106 horizontally placed, the backward and forward direction Z means the body axis direction of the subject laid on the bed 106, i.e., the longitudinal direction of the bed 106, and the right and left direction X means the right and left direction of the subject laid on the bed 106, i.e., the transverse direction of the bed 106.

The gantry control device 112 is a device for controlling revolution and tilt of the gantry 102.

The interlock control device 110 controls the bed control device 111 and the gantry control device 112 according to a command sent from the system control part 120. Further, the interlock control device 110 controls the bed control device 111 and the gantry control device 112, when movement of the bed 106 is directed from an input device (not shown in the drawing) provided in the scanning gantry part 100, such as button or switch.

Further, in order to prevent the subject from contacting with the gantry 102, the interlock control device 110 also calculates interlock on the basis of signals sent from the bed control device 111 and the gantry control device 112. The function of the interlock control device 110 is to calculate interlock on the basis of results of actual movement of the bed 106 or actual tilt of the gantry 102, and differs from that of calculating a movable region shown in the flowchart of FIG. 6 or 8 to be explained later.

The system control part 120 comprises a system control device 121, an image arithmetic device 122, and a storage device 123.

The storage device 123 is a device for storing Raw Data 124 collected by the data acquisition device 108, and is specifically HDD (hard disk drive) or the like.

The image arithmetic device 122 is a device for carrying out an operation for processing the Raw Data 124 stored in the storage device 123 to perform CT image reconstruction.

The system control device 121 is a device for transmitting and receiving data to and from a console control device 203 to be explained later, and controlling the data acquisition device 108, the X-ray control device 109, the interlock control device 110, the image arithmetic device 122, the storage device 123, and so forth.

The console 2 comprises a console display 201 (henceforth simply referred to as "display 201"), a console input device 202 (henceforth simply referred to as "input device 202"), a console control device 203 (henceforth simply referred to as "control device 203"), and a console storage device 204 (henceforth simply referred to as "storage device 204").

The display 201 is a device for displaying a CT image 205, an imaging planning screen, and so forth, and is specifically CRT (cathode-ray tube), liquid crystal display, or the like.

The input device 202 is a device for inputting name of the subject, date and time of investigation, imaging. conditions and so forth, and is specifically a keyboard or a pointing device. The display 201 and the input device 202 may be constituted as one piece of device, for example, a touch panel.

The storage device 204 is a device for storing a CT image 205 created by the image arithmetic device 122.

Hereafter, outline of the operations of the X-ray CT apparatus 1 will be explained.

The X-ray tube 101 irradiates the subject with X-rays according to a direction from the input device 202, X-rays radiated from the X-ray tube 101 and penetrating the subject are detected by the X-ray detector 107 with many X-ray detecting elements, and the data acquisition device 108 measures distribution of transmitted X-rays to collect a reference image. The reference image is displayed on the display 201. The reference image is used by a user as a reference for setting of FOV or imaging position.

The control device 203 calculates a movable region of the bed 106 and imageable region. The control device 203 also transmits information such as movement destination of the bed 106 and tilt angle of the gantry 102 inputted from the input device 202 to the interlock control device 110 to tilt the gantry 102 and move the bed 106. The movable region of the bed 106 is calculated in consideration of size of the subject. For example, size of the subject (body width, body thickness etc.) can be calculated from the reference image or the like, or values stored beforehand or inputted values can be used as the size. Further, the movement destination of the bed 106 transmitted to the interlock control device 110 is set to be within the movable region calculated by the control device 203.

Further, the X-ray control device 109 controls the electric power applied to the X-ray tube 101 according to the imaging conditions inputted from the input device 202, especially X-ray tube voltage, X-ray tube current, etc., so that the X-ray tube 101 irradiates the subject with X-rays corresponding to the imaging conditions. The X-ray detector 107 detects X-rays radiated from the X-ray tube 101 and penetrating the subject with many X-ray detecting elements, and the data acquisition device 108 measures distribution of the transmitted X-rays.

The gantry 102 is controlled by the gantry control device 112, and revolves according to the imaging conditions inputted from the input device 202, especially revolving speed etc. The bed 106 is controlled by the bed control device 111, and moves according to the imaging conditions inputted from the input device 202, especially helical pitch etc.

As the irradiation with X-rays from the X-ray tube 101 and the measurement of the transmitted X-ray distribution by the X-ray detector 107 are repeated with the revolution of the gantry 102, X-ray dose data are obtained for various angles. The obtained X-ray dose data are gathered as Raw Data 124, and transmitted to the image arithmetic device 122. The image arithmetic device 122 reconstructs the CT image 205 by carrying out a back-projection processing of Raw Data 124. The CT image 205 is displayed on the display 201.

Hereafter, embodiments of the present invention will be explained on the basis of the configuration of the X-ray CT apparatus described above.

First Embodiment

The X-ray CT apparatus of this embodiment comprises the gantry 102 that has the opening 105 and can be tilted with respect to the vertical direction, and the bed 106 that can move in the opening of the gantry 102, and further comprises a reference image acquisition unit (X-ray tube 101, X-ray detector 107, data acquisition device 108) that irradiates the subject placed on the bed with X-rays to collect a reference image, a movable region calculating unit (control device 203) that calculates a movable region of the bed on the basis of positional information of the bed, gantry tilt angle, and size of the subject, a movement destination setting unit (control device 203, input device 202) that sets a movement destination of the bed within the movable region calculated by the movable region calculating unit, and a display unit (display 201) that displays the movable region of the bed and/or the movement destination of the bed set by the movement destination setting unit together with the reference image.

An example of this embodiment will be explained below, in which the movable region calculating unit calculates a movable region for the transverse direction, and sets a movement destination for the transverse direction.

According to the first embodiment, a user (medical practitioner, inspection engineer etc.) uses a scanogram 301 for the coronal direction as a reference image, and sets a transverse movement destination 302 of the bed 106 to obtain the CT image 205. The first embodiment will be explained below with reference to FIGS. 2 to 7.

Figure 2:
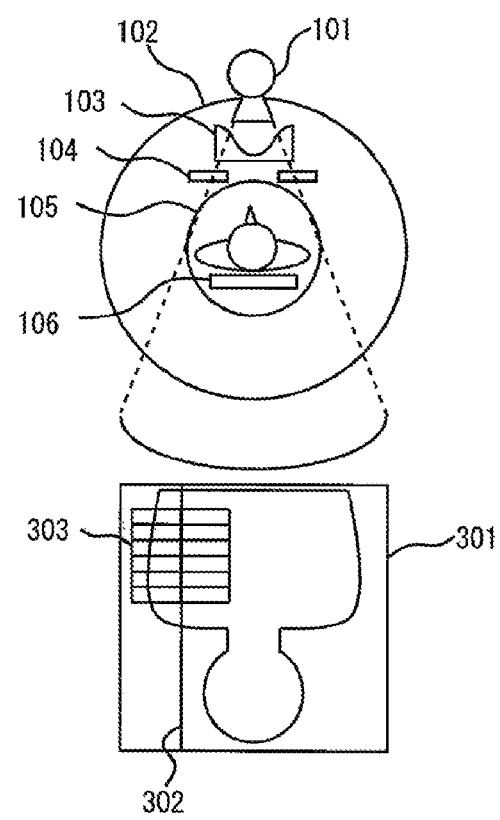
FIG. 2 shows an example of setting of a transverse movement destination of the bed on a scanogram for the coronal direction.

The user obtains the scanogram 301 for the coronal direction in positioning conducted before performing the main imaging. And as shown in FIG. 2, the display 201 displays the scanogram 301 for the coronal direction. The display 201 further displays a mark 302 indicating the transverse movement destination (henceforth simply referred to as transverse movement destination 302) and a mark 303 indicating FOV (field of view, henceforth simply referred to as FOV 303) superimposed on the scanogram 301 for the coronal direction. The user sets an appropriate transverse movement destination of the bed 106 by changing the position of the transverse movement destination 302 displayed on the display 201 by using the input device 202. Further, the user sets an appropriate FOV by changing the position and size of FOV 303 displayed on the display 201 by using the input device 202.

The transverse movement destination of the bed is restricted by height of the bed 106 and tilt angle of the gantry 102.

Specifically, transversely movable distance of the bed 106 changes depending on the height of the bed 106. As shown in FIG. 3, a transversely movable distance (1) for a case where the height of the bed 106 corresponds to the height of the center of the opening 105 is larger than a transversely movable distance (2) for a case where the height of the bed 106 is lower than the height of the center of the opening 105. Similarly, the transversely movable distance (1) for a case where the height of the bed 106 corresponds to the height of the center of the opening 105 is larger than a transversely movable distance (2) for a case where the height of the bed 106 is higher than the height of the center of the opening 105. In other words, as the height of the bed 106 deviates from the height of the center of the opening 105, the transversely movable distance of the bed 106 becomes smaller. Therefore, the user needs to set the transverse movement destination of the bed 106 in consideration of the height of the bed 106.

Further, the transversely movable distance of the bed 106 also changes depending on the tilt angle of the gantry 102. As shown in FIG. 4, a transversely movable distance (1) for a case where the gantry 102 is not tilted (tilt angle θ is 0°) is larger than a transversely movable distance (2) for a case where the gantry 102 is tilted (tilt angle θ is not 0°). This is similarly applied to a case where the gantry 102 is tilted forward (tilt angle θ is larger than 0°) and a case where the gantry 102 is tilted backward (tilt angle θ is smaller than 0°). In other words, the transversely movable distance of the bed 106 becomes smaller as absolute value of the tilt angle of the gantry 102 becomes larger. Therefore, the user needs to set the transverse movement destination of the bed 106 in consideration of the tilt angle of the gantry 102.

If the user sets the transverse movement destination of the bed 106 without taking the height of the bed 106 and the tilt angle of the gantry 102 into consideration, the subject may contact with the gantry 102 when the bed 106 is actually moved. In such a case, it becomes necessary for the user to reinput the transverse movement destination of the bed 106 or change the position of the subject and perform imaging for obtaining the scanogram 301 again.

Therefore, when the transverse movement destination is set by using the scanogram 301 for the coronal direction as a reference image, the control device 203 calculates a transversely movable region of the bed 106 beforehand from the height of the bed 106 and the tilt angle of the gantry 102, and restricts input of the user so that the transverse movement destination should not be out of the transversely movable region of the bed 106. Further, if needed, the display 201 superimposes the transversely movable region 304 on the scanogram 301 and displays the superimposed region 304 on the scanogram 301.

Figure 5:
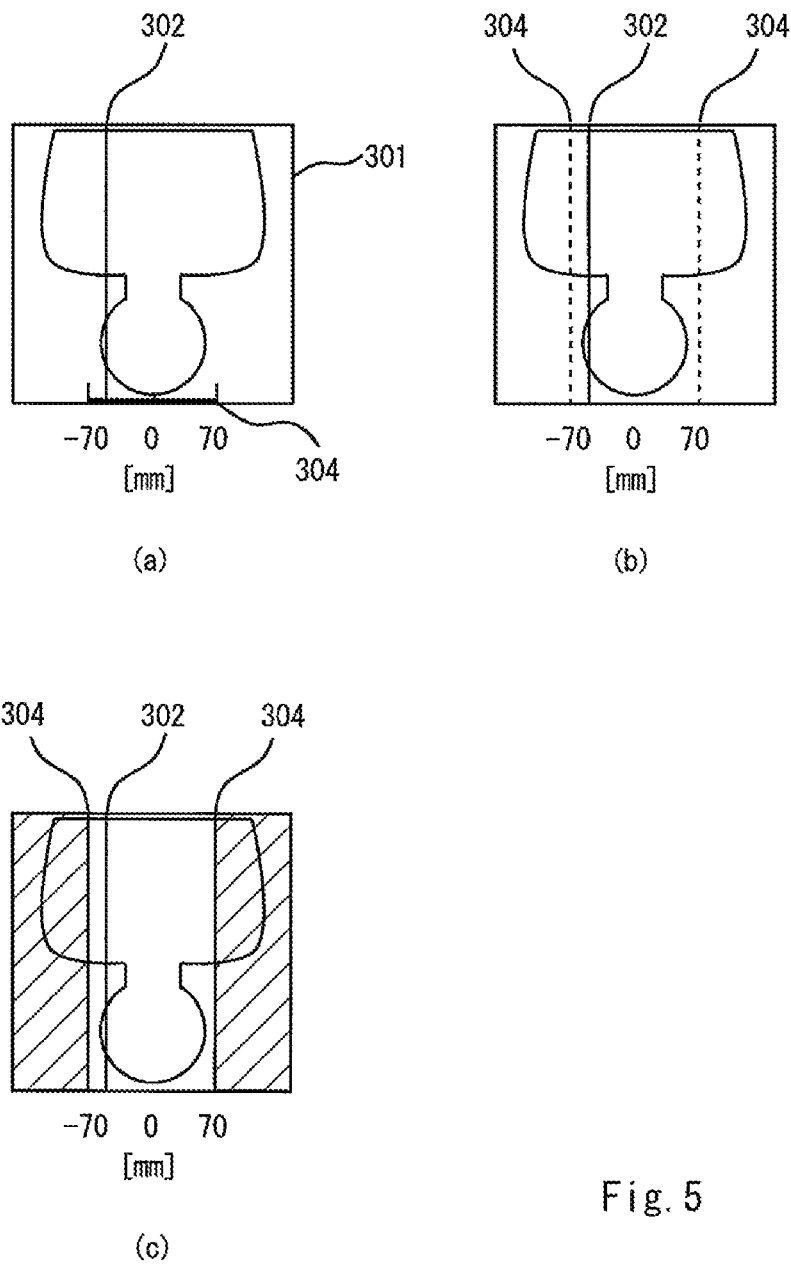
FIG. 5 shows examples of display of transversely movable region on a scanogram for the coronal direction.

FIG. 5 shows three examples of display of the transversely movable region 304. In each of FIGS. 5, (a) to (c), the transverse movement destination 302 and the transversely movable region 304 are superimposed and displayed on the scanogram 301. Further, in each of FIG. 5, (a) to (c), there are displayed the left end position (−70 mm in the examples shown in FIG. 5) from the current position (or default position) of the bed 106 as the starting point and the right end position (70 mm in the examples shown in FIG. 5) from the same of the transversely movable region 304.

In FIG. 5, (a), the transversely movable region 304 is shown in the lower part of the scanogram 301 is displayed as "bar display". In the example shown in FIG. 5, (a), divisions are given at the current position (or default position) of the bed 106, and the left end position and the right end position of the transversely movable region 304.

In FIG. 5, (b), the left end position and right end position of the transversely movable region 304 are indicated with lines ("dotted lines" in the example shown in FIG. 5, (b)) of a kind different from that of the line indicating the transverse movement destination 302 ("solid line" in the example shown in FIG. 5, (b)).

In FIG. 5, (c), regions that are not the transversely movable region 304 are indicated with a predetermined pattern (hatching in the example shown in FIG. 5, (c)). In other words, the left end position and the right end position of the transversely movable region 304 are indicated as boundary lines of the regions having the predetermined pattern and the region not having the predetermined pattern.

Operations of the X-ray CT apparatus 1 of the first embodiment will be explained with reference to FIG. 6.

First, in Step S101, the X-ray CT apparatus 1 performs imaging for obtaining the scanogram 301. Specifically, the imaging is performed by irradiating the subject with X-rays from the X-ray tube 101, with moving the bed 106 along the body axis direction under control by the bed control device 111. The obtained scanogram 301 is stored in the storage device 204. Further, positions of the bed 106 for the up and down direction and right and left direction and the tilt angle of the gantry 102 at the time of the imaging for obtaining the scanogram 301 are also stored in the storage device 204.

Then, in Step S102, the control device 203 reads out the scanogram 301 from the storage device 204, and displays it on the display 201. Further, the control device 203 also superimposes FOV 303 on the scanogram 301 and displays the FOV 303 on the display 201 with the scanogram 301.

Then, in Step S103, the control device 203 calculates the transversely movable region 304 on the basis of the "positions of the bed 106 for the up and down direction and the right and left direction, and the tilt angle of the gantry 102 at the time of the imaging for obtaining the scanogram 301", which are stored in the storage device 204, and results of image analysis of the scanogram 301.

Specifically, the control device 203 calculates body width of the subject on the basis of the image analysis of the scanogram 301 performed by the image arithmetic device 122. Further, the control device 203 applies the calculated body width of the subject to, for example, a "human body model (ellipse model etc.)" stored in the storage device 204 beforehand to estimate size of the subject (maximum body width, maximum body thickness etc.). Then, the control device 203 calculates a region in which the bed 106 can move along the transverse direction without contact of the subject with the gantry 102, i.e., a transversely movable region 304 of the bed

106, on the basis of the positions of the bed 106 for the up and down and right and left directions at the time of obtaining the scanogram 301, tilt angle of the gantry 102 at the time of obtaining the scanogram 301, estimated size of the subject, and size of the top of the bed 106 stored beforehand.

In the following steps, when up and down and right and left movement destinations of the bed 106, tilt angle of the gantry 102 and so forth are specified, the control device 203 calculates the transversely movable region 304 of the bed 106 again on the basis of the specified values.

As the size of the subject (maximum body width, maximum body thickness etc.), values stored in the storage device 204 beforehand may be used, or values inputted by using the input device 202 may be used.

Then, in Step S104, the control device 203 superimposes the transversely movable region 304 calculated in Step S103 with the scanogram 301 and displays it on the display 201 with the scanogram 301. The user may be allowed to select whether the calculated transversely movable region 304 is displayed on the display 201 or not.

If the transversely movable region 304 is displayed on the display 201, the user can easily confirm whether an objective site of imaging can be disposed at the center of the opening 105 by visual inspection.

Then, in Step S105, if the user moves the transverse movement destination 302 by using the input device 202 such as a pointing device, the control device 203 sets the transverse movement destination of the bed 106 on the basis of moved distance of the transverse movement destination 302. Further, the user may input moving distance (for example, 20 mm etc.) of the bed 106 for the transverse direction by using the input device 202 such as a keyboard. In any case, the control device 203 judges whether the set transverse movement destination is within the transversely movable region 304. If it is in the transversely movable region 304, it determines that it can be set, and if it is outside the transversely movable region 304, it determines that it cannot be set.

When the transversely movable region 304 is displayed on the display 201, the user can specify the transverse movement destination of the bed 106 with confirming the transversely movable region 304.

Then, in Step S106, the control device 203 superimposes the transverse movement destination 302 set according to the values set in Step S105 on the scanogram and displays it on the display 201 with the scanogram 301. If the user moves the transverse movement destination 302 displayed on the screen by using the input device 202 such as a pointing device, this operation itself serves as an input operation, and therefore input and display are continuously repeated. Further, when the user inputs distance of transverse movement of the bed 106 by using the input device 202 such as a keyboard, if the user pushes a display button by using the input device 202, for example, the transverse movement destination 302 is displayed again at the specified position.

Then, in Step S107, the bed 106 is moved, and the gantry 102 is tilted under the control by the system control device 121.

Specifically, the control device 203 transmits the transverse movement destination of the bed 106 set in Step S105, the position of the bed 106 for the up and down direction and the tilt angle of the gantry 102 at the time of obtaining the scanogram 301 to the system control device 121. The system control device 121 transmits the transverse movement destination of the bed 106, the position for up and down direction (height) of the bed 106, and the tilt angle of the gantry 102 to the interlock control device 110. The interlock control device 110 transmits the transverse movement destination of the bed 106 to the bed control device 111, and transmits the tilt angle of the gantry 102 to the gantry control device 112. The bed control device 111 moves the bed 106 to the specified transverse movement destination. Further, the gantry control device 112 tilts the gantry 102 at the specified tilt angle.

Then, in Step S108, imaging of the subject is performed under the control by the system control device 121 to create the CT image 205. The procedure up to the creation of the CT image 205 is as described above. The created CT image 205 is correlated with the scanogram 301, and stored in the storage device 204. Further, positions of the bed 106 for up and down and right and left directions, and the tilt angle of the gantry 102 at the time of obtaining the CT image 205 are also stored in the storage device 204.

The control device 203 can display the positions of the bed 106 for up and down and right and left directions, and the tilt angle of the gantry 102 at the time of obtaining the CT image 205 on the display 201, together with the CT image 205 and the scanogram 301. On the basis of information of these items, the user can judge whether the region to be imaged has been imaged or not.

As described above, in the first embodiment, the transverse movement destination of the bed 106 is set in the transversely movable region 304. Therefore, when the bed 106 is actually moved, contact of the subject with the gantry 102 is surely avoided, and there is no relapse of the procedure such as reacquisition of the scanogram 301 or reinput of the transverse movement destination of the bed 106.

Furthermore, when the transversely movable region 304 is displayed on the display 201, the user can specify the transverse movement destination of the bed 106 with confirming the transversely movable region 304, and thus usability can be improved.

Second Embodiment

The X-ray CT apparatus of this embodiment is characterized by having a function of calculating an imageable region according to filter size, and displaying it. That is, the X-ray CT apparatus of the second embodiment comprises a reference image acquisition unit that collects a reference image by irradiating a subject placed on the bed 106 with X-rays (X-ray tube 101, X-ray detector 107, data acquisition device 108), a movable region calculating unit that calculates a transversely movable region of the bed on the basis of height of the bed 106 and size of the subject, and/or calculates an up and down movable region of the bed on the basis of position of the bed for the transverse direction and size of the subject (control device 203), a movement destination setting unit that sets a movement destination of the bed in the transversely movable region and/or the up and down movable region calculated by the movable region calculating unit (control device 203, input device 202), a filter size setting unit that sets size of a filter for adjusting radiation intensity of the X-rays (input device 202), an imageable region calculating unit that calculates an imageable region on the basis of a movement destination of the bed set by the movement destination setting unit and a filter size set by the filter size setting unit (control device 203), and a displaying unit that displays the imageable region calculated by the imageable region calculating unit superimposed on the reference image.

Hereafter, an example in which the movable region calculating unit calculates the transversely movable region and sets the transverse movement destination will be explained.

In the second embodiment, the user uses the scanogram 301 for the coronal direction as a reference image, sets size of the bow tie filter 103 and the transverse movement destination of the bed 106, and sets FOV (reconstruction region) by confirming the imageable region 305 to obtain the CT image 205. The second embodiment will be explained below with reference to FIGS. 7 to 9. The same elements as those of the aforementioned embodiment are indicated with the same numerals, and explanations thereof are omitted.

Figure 7:
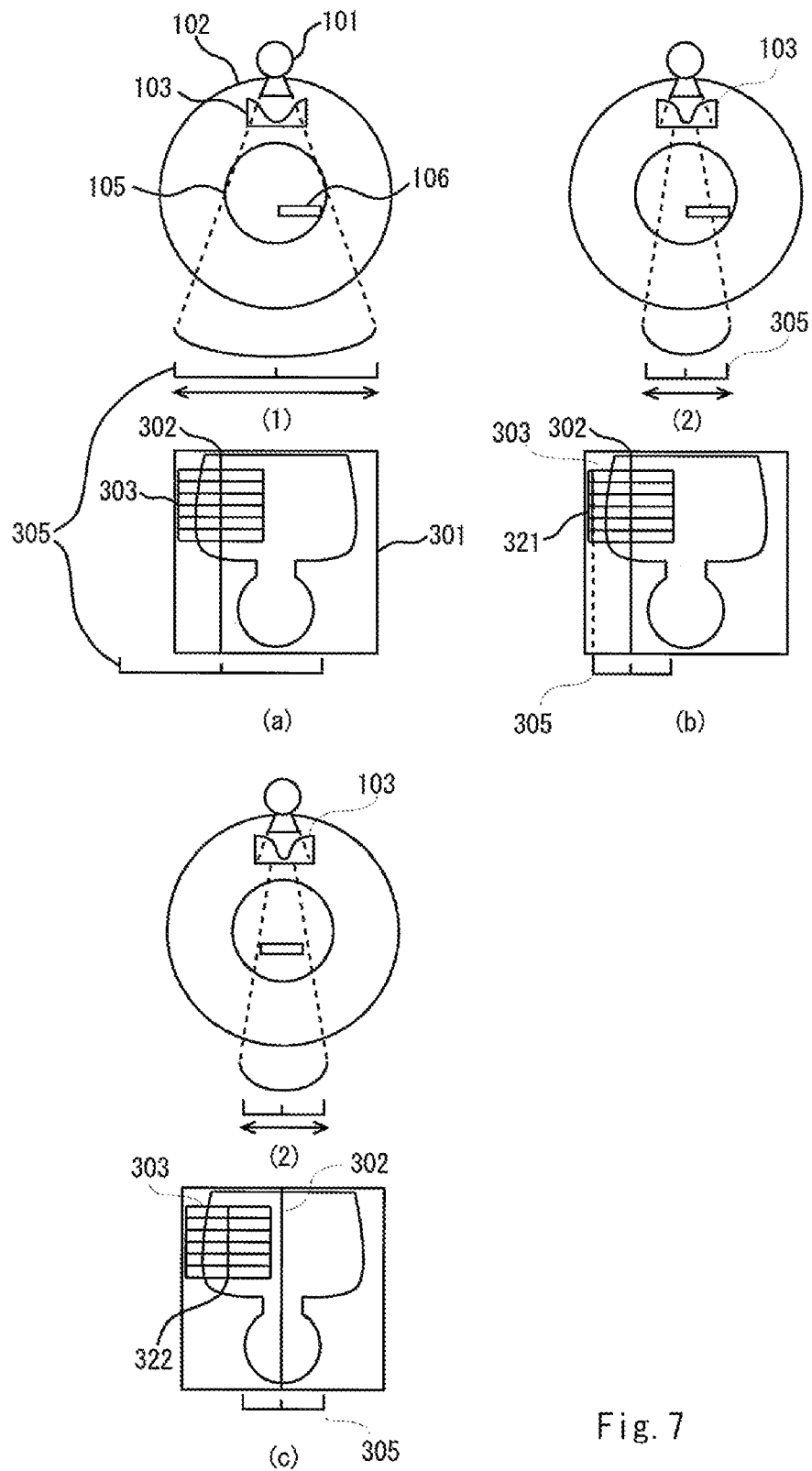
FIG. 7 shows imageable region (1) for the case where a large bow tie filter is used, and imageable region (2) for the case where a small bow tie filter is used.

The imageable region 305 changes depending on the size of the bow tie filter 103. FIG. 7, (a) shows an example where the size of the bow tie filter 103 is large (for example, bow tie filter 103 for the whole body). FIG. 7, (b) and (c) show an example where the size of the bow tie filter 103 is small (for example, bow tie filter 103 for the heart).

In the case of FIG. 7, (a), the X-rays radiated from the X-ray tube 101 pass though the bow tie filter 103 without decaying so much, and are irradiated on the subject. The irradiation region at this time corresponds to the imageable region 305 shown in FIG. 7, (a). As explained for the first embodiment, the bed 106 is moved according to the set transverse movement destination at the time of obtaining the CT image 205, and therefore the imageable region 305 is a region of which center is the transverse movement destination 302. Accordingly, a region to be imaged and a region not to be imaged exist within the scanogram 301. In FIG. 7, (a), the set FOV 303 is within the imageable region 305, and therefore the CT image 205 can be reconstructed for the width of this FOV 303.

In the case of FIG. 7, (b), X-rays radiated from the X-ray tube 101 in the circumferential part of the irradiation field are decayed by the bow tie filter 103, and the irradiation field is narrowed. Therefore, the imageable region 305 becomes narrower than that shown in FIG. 7, (a). In FIG. 7, (b), the set FOV 303 is not within the imageable region 305, and a region 321 outside the imageable region exists in the region of FOV 303. Therefore, the CT image 205 cannot be reconstructed for the width of this FOV 303. Then, in order to obtain an image of the objective site, it is necessary to use a bow tie filter 103 of a larger size, but the user cannot known how much extent the bow tie filter 103 needs to be enlarged in order that the objective site is included in the imageable region 305.

Further, the position of the imageable region 305 changes depending on the transverse movement destination of the bed 106. Therefore, the CT image 205 may not be reconstructed at the set position of FOV 303. In such a case, whether the objective site can be imaged or not cannot be judged until FOV 303 is inputted, and when imaging cannot be performed with the set FOV 303, reinput of FOV 303 or reacquisition of the scanogram 301 becomes necessary thereafter.

Therefore, in the second embodiment, a mark indicating the imageable region 305 (henceforth the term imageable region 305 includes the mark) is displayed on a screen displaying the reference image, and when the user moves the transverse movement destination 302 from the position shown in FIG. 7, (b) to the position shown in FIG. 7, (c) by using the input device 202, the control device 203 changes the position of the imageable region 305 so that it follows the position of the transverse movement destination 302, and displays it on the display 201. In FIG. 7, (c), the center of FOV 322 having been hidden by the transverse movement destination 302 in FIG. 7, (b) is also displayed.

Further, the control device 203 calculates width and position of the imageable region 305 beforehand on the basis of the size of the bow tie filter 103 and the position of the transverse movement destination 302, and superimposes the imageable region 305 on the scanogram and displays it on the display 201 with the scanogram 301. Furthermore, if needed, the control device 203 superimposes switchable sizes of the bow tie filter 103 on the scanogram 301 and displays it on the display 201.

Operations of the X-ray CT apparatus 1 of the second embodiment will be explained with reference to FIG. 8.

Figure 6:
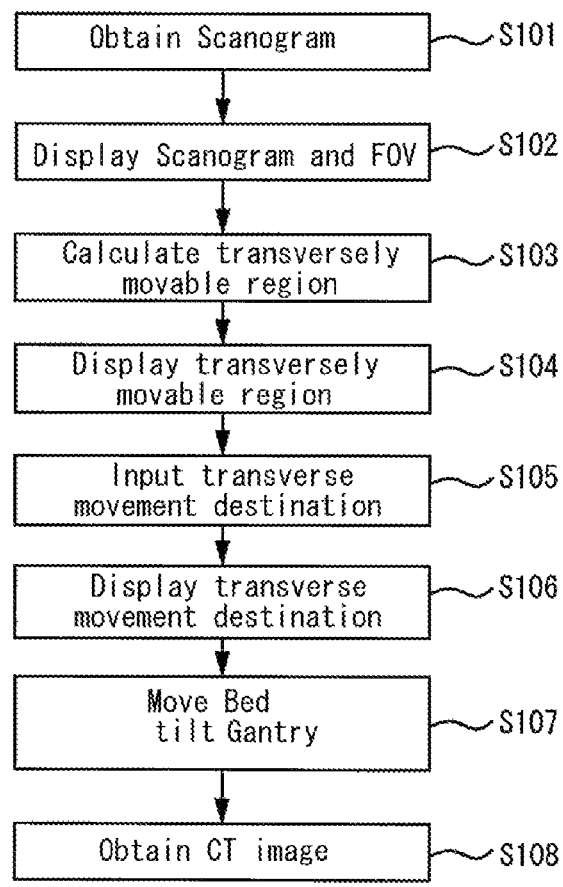
FIG. 6 is a first flowchart showing operations of an X-ray CT apparatus.

Steps S101 to S104 are the same as those shown in FIG. 6. A scanogram is obtained and displayed together with FOV, and a transversely movable region is calculated and displayed (S101-S104).

Then, in Step S201, when the user inputs size of the bow tie filter 103 by using the input device 202, the control device 203 sets the inputted size of the bow tie filter 103. The control device 203 may automatically set the size of the bow tie filter 103 according to imaging region (for example, "whole body", "heart", etc.). The set size of bow tie filter 103 is temporarily stored in RAM or the storage device 204.

Steps S105 and S106 are the same as those shown in FIG. 6. The transverse movement destination is imputed and displayed (S105, S106).

Then, in Step S202, the control device 203 calculates width and position of the imageable region 305 on the basis of the size of the bow tie filter 103 inputted in Step S201, and the position of the transverse movement destination 302 inputted in Step S105.

Then, in Step S203, the control device 203 superimposes the imageable region 305 calculated in Step S202 on the scanogram 301 and displays it on the display 201.

FIG. 9, (a) to (c) show examples of display of the imageable region 305. In all of FIG. 9, (a) to (c), the transverse movement destination 302, FOV 303, and the transversely movable region 304 are displayed superimposed on the scanogram 301.

In the example shown in FIG. 9, (a), the control device 203 superimposes a single imageable region 305 calculated on the basis of size of a single bow tie filter 103 inputted in Step S201 on the scanogram 301 and displays it on the display 201.

Further, in FIG. 9, (b) and (c), the control device 203 displays, in addition to the imageable region 305 corresponding to the size of the bow tie filter 103 inputted in Step S201, imageable regions 305 corresponding to other sizes of the bow tie filter 103 superimposed on the scanogram 301 on the display 201.

In FIG. 9, (a), in order to show the imageable region 305, the non-imageable region 321 is displayed as transparent display or texture display. In FIG. 9, (a), predetermined transparent display or texture display is schematically shown with "oblique lines".

In FIG. 9, (b), borders of a plurality of the imageable regions 305 and the non-imageable regions 321 are indicated with straight lines of different types.

In FIG. 9, (b), borders b1, b2 and b3 of the imageable regions 305 and the non-imageable regions 321 corresponding to three kinds of sizes of the bow tie filter 103 are indicated. Specifically, borders b1 of the imageable region 305 and the non-imageable regions 321 corresponding to the size of the smallest bow tie filter 103 are indicated with "dotted lines". Further, borders b2 of the imageable region 305 and the non-imageable regions 321 corresponding to the size of the bow tie filter 103 of middle size are indicated with "dashed lines". Furthermore, a border b3 of the imageable region 305 and the non-imageable region 321 corresponding to the size of the largest bow tie filter 103 are indicated with "alternate long and short dash lines".

In FIG. 9, (c), in order to indicate a plurality of imageable regions 305, the non-imageable regions 321 are indicated with different gradations of transparent display or texture display. In FIG. 9, (c), the different gradations of predetermined transparent display or texture display are schematically distinguished by difference in numbers of "oblique lines".

In the example shown in FIG. 9, (c), the non-imageable regions 321 corresponding to three kinds of the sizes of the bow tie filter 103 are shown. Specifically, the non-imageable regions 321-1 corresponding to the size of the smallest bow tie filter 103 are shown with the smallest number of "oblique lines". Further, the non-imageable regions 321-2 corresponding to the size of the bow tie filter 103 of the middle size are shown with a middle number of "oblique lines". Furthermore, the non-imageable region 321-3 corresponding to the size of the largest bow tie filter 103 is shown with the largest number of "oblique lines".

Figure 8:
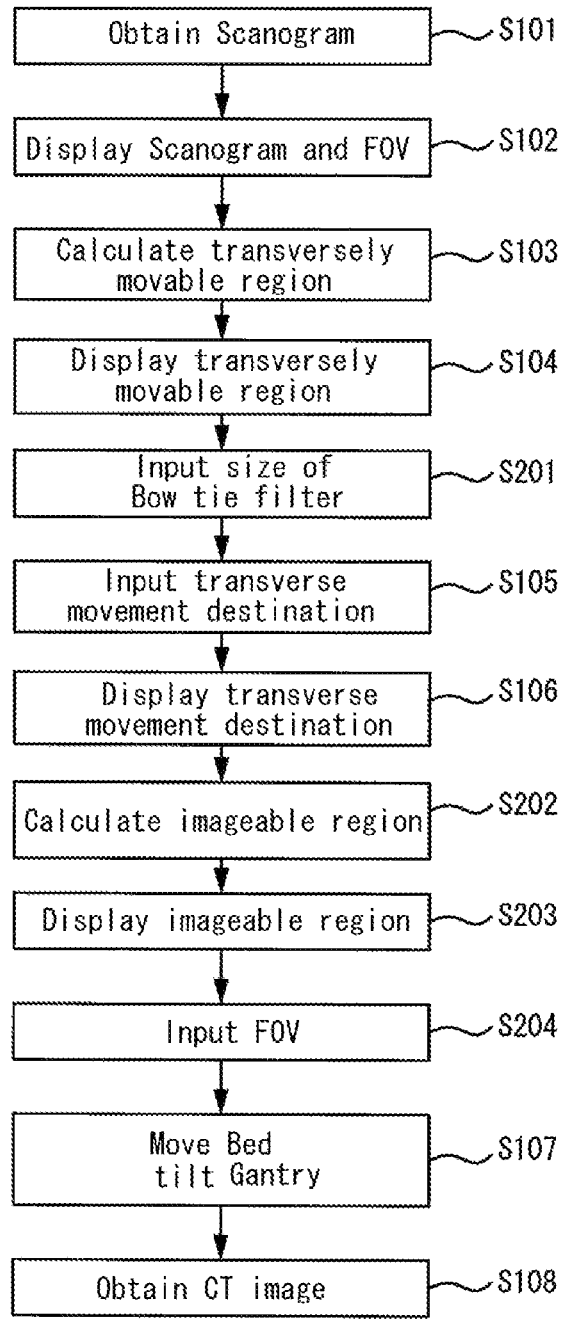
FIG. 8 is a second flowchart showing operations of an X-ray CT apparatus.

The explanation returns to FIG. 8.

In Step S204, when the user inputs FOV 303 by using the input device 202, the control device 203 sets width and position of the inputted FOV 303, and superimposes and displays them on the screen displaying the reference image.

Steps S107 and S108 are the same as those shown in FIG. 6. The bed 106 is moved to a set position and the gantry 102 is tilted by a set angle (S107), and CT image is obtained (S108). When the bow tie filter 103 is changed, if it is changed simultaneously with moving the bed 106 in Step S107, investigation time can be shortened.

In the second embodiment, as shown in FIG. 9, the imageable region 305 corresponding to the inputted size of the bow tie filter 103 is superimposed and displayed on the scanogram 301, and therefore the user can input FOV 303 with confirming whether an objective site of imaging is included in the imageable region 305.

Further, by displaying, in addition to the imageable region 305 corresponding to the inputted size of the bow tie filter 103, the imageable regions 305 corresponding to other sizes of the bow tie filter 103 superimposed on the scanogram 301, even when the objective site of imaging is not included in the imageable region 305 corresponding to the size of the specified bow tie filter 103, the user can easily judge to which size the bow tie filter 103 must be changed on the basis of visual inspection.

As described above, the imageable region 305 can be known before input of FOV 303, therefore whether an objective site can be imaged or not can be easily judged, and the usability can be improved.

In addition, when a plurality of sites are imaged, a transverse movement destination may be inputted for every site, and the imageable region 305 may be displayed for each.

Further, although FOV 303 is inputted after the transverse movement destination of the bed 106 is inputted in the above explanation, the transverse movement destination of the bed 106 may be inputted after FOV 303 is inputted. Further, after FOV 303 is inputted, the control device 203 may set the transverse movement destination of the bed 106 so that the transverse movement destination corresponds to the center 322 of FOV.

Third Embodiment

In the X-ray CT apparatus of this embodiment, the movable region calculating unit has a function of calculating an up and down movable region of the bed and setting an up and down movement destination.

In the third embodiment, the user uses the scanogram 301 for the sagittal direction or an axial image (scanning image) as a reference image, sets size of the bow tie filter 103 and an up and down movement destination of the bed 106, and sets FOV 303 by confirming the imageable region 305 to obtain the CT image 205. The third embodiment will be explained below with reference to FIGS. 10 and 11. The same elements as those of the aforementioned embodiments are indicated with the same numerals, and explanations thereof are omitted. In particular, flow of the operations of the X-ray CT apparatus 1 is the same as that of the second embodiment.

First, the method of using the scanogram 301 for the sagittal direction as a reference image will be explained. The scanogram 301 for the sagittal direction is created by rotating the X-ray tube 101 by 90° along the gantry 102 to irradiate the subject with X-rays from the side of the subject. In the scanogram 301 for the sagittal direction, the subject on the Y-Z plane direction is viewed, which is different from that of the coronal direction, and therefore it is used for setting of up and down movement of the bed 106, not right and left movement of the bed 106. The up and down movement destination is restricted by position of the bed for the transverse direction and gantry tilt angle.

Figure 10:
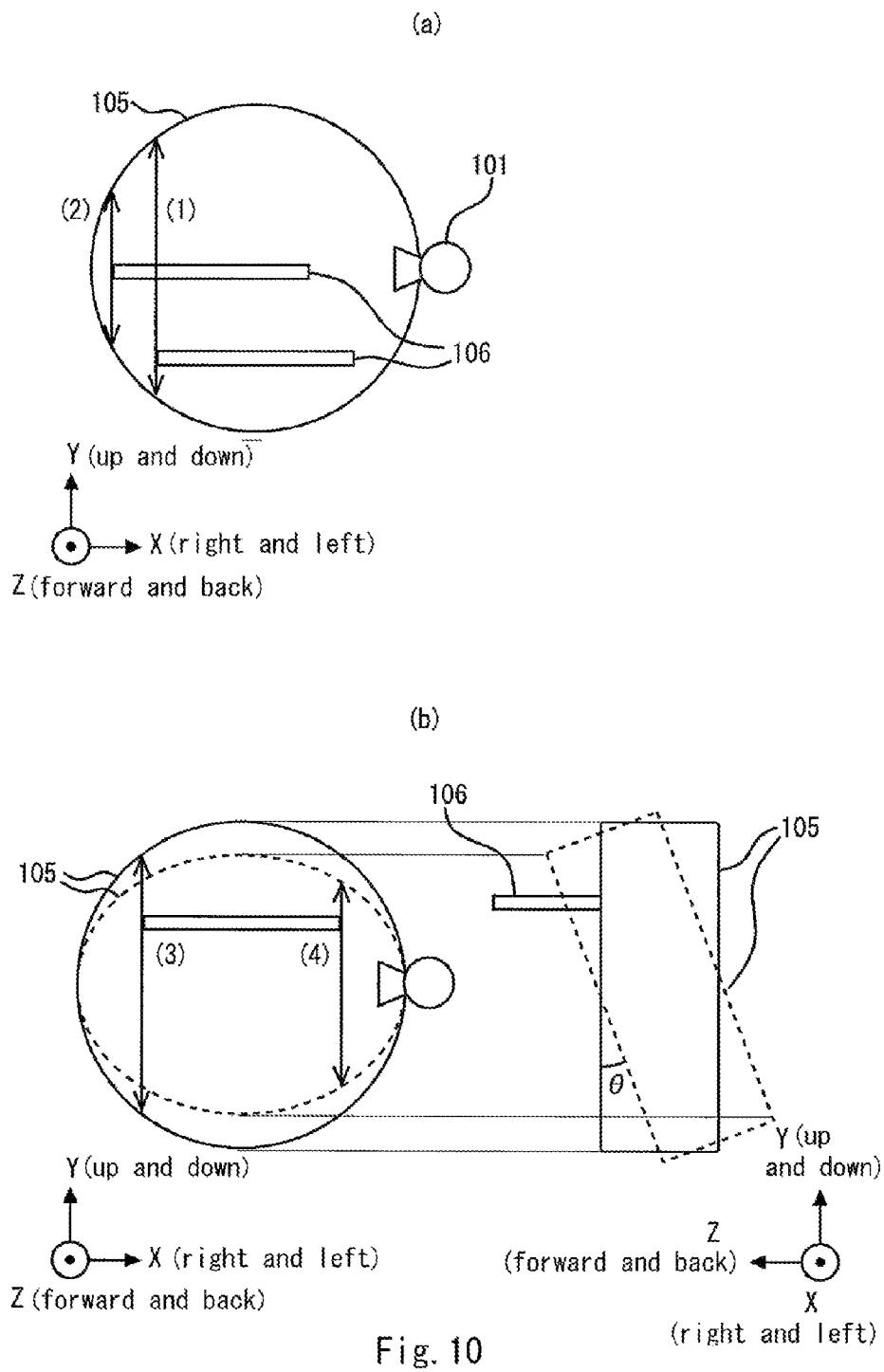
FIG. 10, (a) shows up and down movable distance (1) for the case where the position of the side of the bed corresponds to the height of the center of the opening, and up and down movable distance (2) for the case where the position of the side of the bed does not correspond to the height of the center of the opening, and (b) shows up and down movable distance (3) for the case where the gantry is not tilted, and up and down movable distance (4) for the case where the gantry is tilted.

Specifically, up and down movable distance of the bed 106 changes depending on the position of the bed 106 for the transverse direction (position for the X direction). As shown in FIG. 10, (a), an up and down movable distance (1) for a case where position of the bed 106 for the transverse direction (position for the X direction) corresponds to the position of the center of the opening 105 is larger than an up and down movable distance (2) for a case where the position of the bed 106 for the transverse direction (position for the X direction) deviates from the center of the opening 105. In other words, as the position of the bed 106 for the transverse direction (position for the X direction) deviates from the center of the opening 105, the up and down movable distance of the bed 106 becomes smaller. Therefore, the user needs to set the up and down movement destination of the bed 106 in consideration of the position of the bed 106 for the transverse direction (position for the X direction).

Further, the up and down movable distance of the bed 106 also changes depending on the tilt angle of the gantry 102. As shown in FIG. 10, (b), an up and down movable distance (3) for a case where the gantry 102 is not tilted (tilt angle θ is 0°) is larger than an up and down movable distance (4) for a case where the gantry 102 is tilted (tilt angle θ is not 0°). This is similarly applied to a case where the gantry 102 is tilted forward (tilt angle θ is larger than 0°) and a case where the gantry 102 is tilted backward (tilt angle θ is smaller than 0°). In other words, the up and down movable distance of the bed 106 becomes smaller as absolute value of the tilt angle of the gantry 102 becomes larger. Therefore, the user needs to set the up and down movement destination of the bed 106 in consideration of the tilt angle of the gantry 102.

Figure 11:
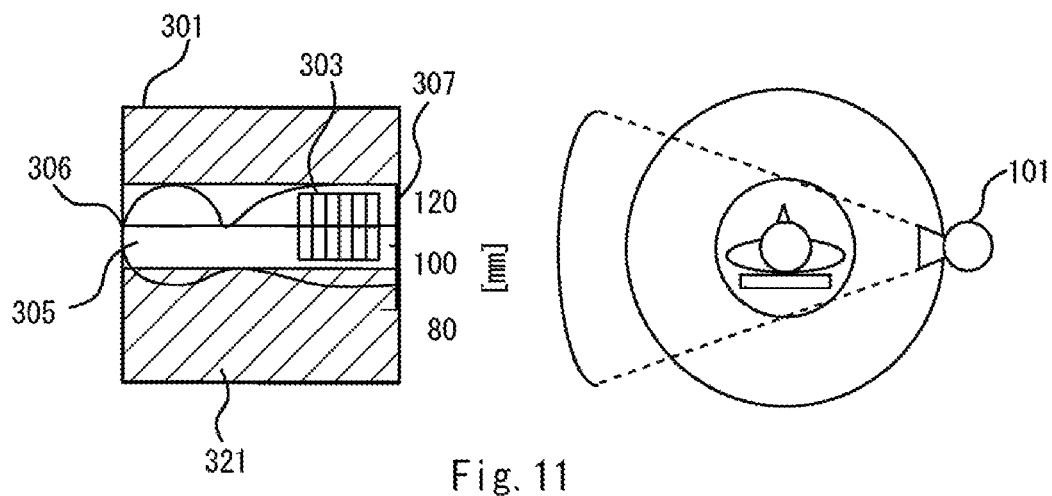
FIG. 11 shows an example of display of up and down movable region and imageable region on a scanogram for the sagittal direction.

Therefore, when the movement destination is set by using the scanogram 301 for the sagittal direction as a reference image, the control device 203 calculates the up and down movable region 307 of the bed 106 beforehand from the position of the bed 106 for the transverse direction (position for the X direction) and the tilt angle of the gantry 102, and restricts input of the user so that the up and down movement destination 306 of the bed 106 set by the user should not be outside the up and down movable region 307. Further, as shown in FIG. 11, if needed, the display 201 displays the up and down movable region 307 and the imageable region 305 (or non-imageable region 321) superimposed on the scanogram 301.

The control device 203 also calculates the up and down movable region 307 of the bed 106 in consideration of size of the subject and size of the top of the bed 106, as in the calculation of the transversely movable region 304 of the bed 106.

The method of using the axial image 301a as a reference image will be explained below. In the axial image 301a, the subject on the X-Y plane is viewed, and therefore transverse movement and up and down movement of the bed 106 can be set by referring to the axial image 301a.

Therefore, when the axial image 301a is used as a reference image, the control device 203 calculates the transversely movable region 304 of the bed 106 beforehand from the height of the bed 106 and the tilt angle of the gantry 102, and restricts input of the user so that the transverse movement destination 302 of the bed 106 set by the user should not be outside the transversely movable region 304. The control device 203 also calculates the up and down movable region 307 of the bed 106 beforehand from the position of the bed 106 for the transverse direction (position for the X direction) and the tilt angle of the gantry 102, and restricts input of the user so that the up and down movement destination 306 of the bed 106 set by the user should not be outside the up and down movable region 307.

Figure 12:
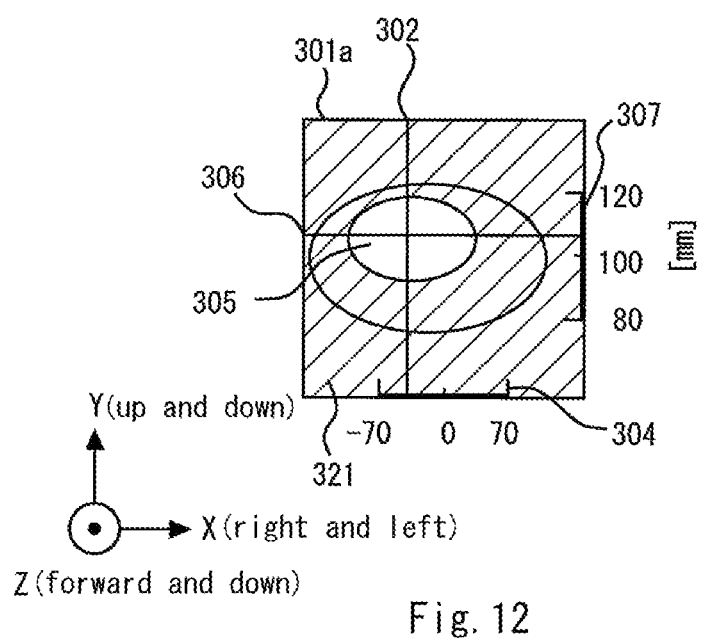
FIG. 12 shows an example of display of transversely movable region, up and down movable region, and imageable region on an axial image.

Further, as shown in FIG. 12, if needed, the display 201 displays the transversely movable region 304, the up and down movable region 307, and the imageable region 305 (or non-imageable region 321) superimposed on the axial image 301a.

In the third embodiment, if the reference image is the scanogram 301 for the sagittal direction, the up and down movement destination 306 of the bed 106 is set within the up and down movable region 307. Therefore, when the bed 106 is actually moved, contact of the subject and the gantry 102 is surely avoided, and there is no relapse of the procedure such as reacquisition of the scanogram 301 or reinput of the up and down movement destination 306 of the bed 106.

Further, if the reference image is the axial image 301a, the transverse movement destination 302 and the up and down movement destination 306 of the bed 106 are set in the transversely movable region 304 and the up and down movable region 307, respectively. Therefore, when the bed 106 is actually moved, contact of the subject and the gantry 102 is surely avoided, and there is no relapse of the procedure such as reacquisition of the scanogram 301 or reinput of the transverse movement destination 302 or the up and down movement destination 306 of the bed 106.

Further, when the up and down movable region 307 is displayed on the display 201, the user can specify the up and down movement destination of the bed 106 with confirming the up and down movable region 307. Furthermore, when the transversely movable region 304 and the up and down movable region 307 are displayed on the display 201, the user can specify the transverse movement destination 302 and the up and down movement destination 306 of the bed 106, with confirming the transversely movable region 304 and the up and down movable region 307.

When both the scanogram 301 for the coronal direction and the scanogram 301 for the sagittal direction are used as reference images, the transversely movable region 304 can be superimposed and displayed on the scanogram 301 of the coronal direction, and the up and down movable region 307 can be displayed and superimposed on the scanogram 301 for the sagittal direction.

Fourth Embodiment

This embodiment is characterized by GUI (graphic user interface) for a user at the time of setting the movement destination of the bed by using the input device 201 and the display 202. That is, in the fourth embodiment, the user can move a reference image displayed on the display 202, and the movement destination of the bed 106 is set by this operation of moving the reference image. The fourth embodiment will be explained below with reference to FIG. 13. The same elements as those of the aforementioned embodiments are indicated with the same numerals, and explanations thereof are omitted. In particular, flow of the operations of the X-ray CT apparatus 1 is the same as that of the second embodiment.

First, the case of using the scanogram 301 for the coronal direction is used as a reference image is explained.

Figure 13:
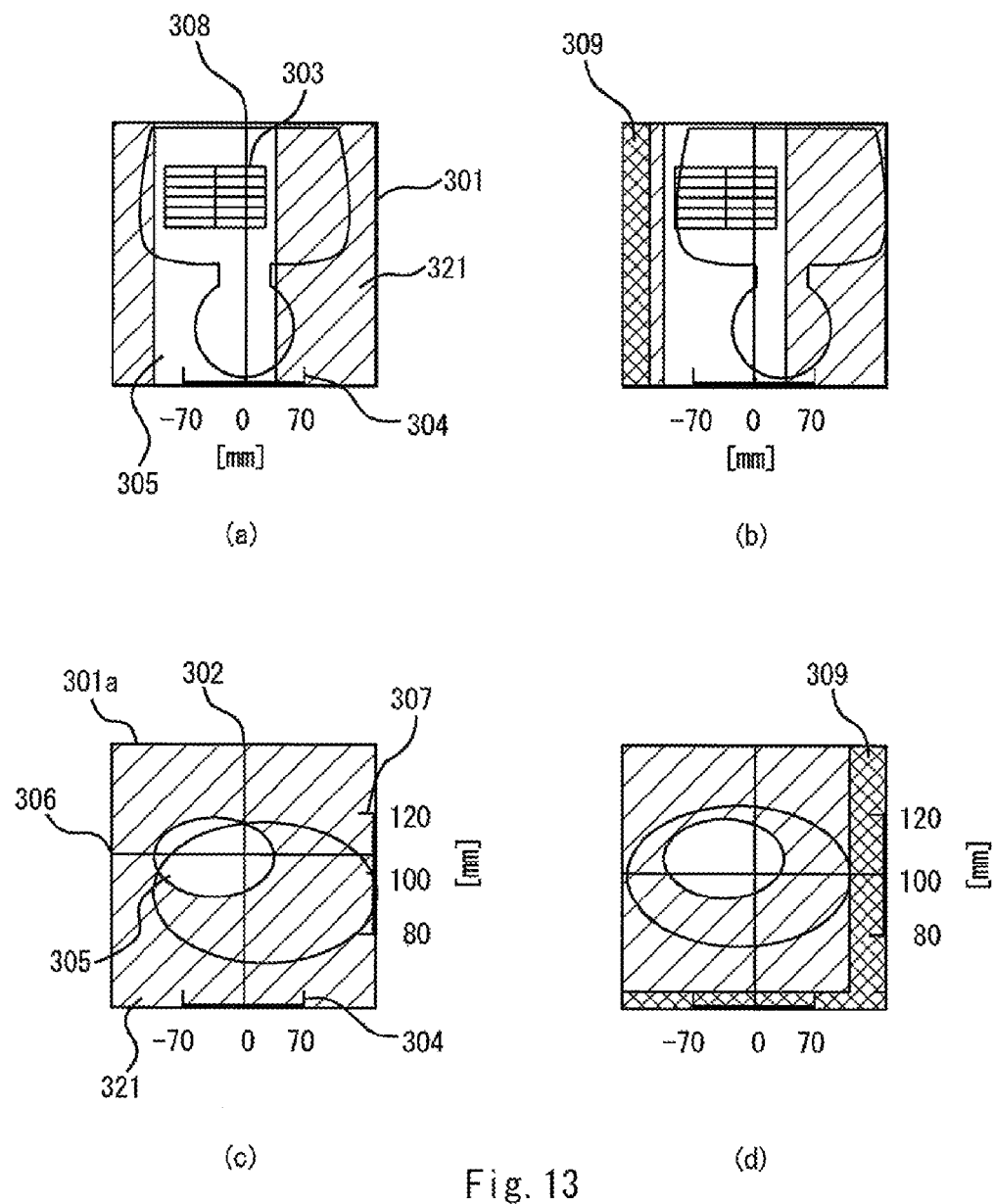
FIG. 13 includes drawings for explaining an example of specifying a movement destination of the bed by moving a reference image FIG. 14 includes drawings for explaining an example of specifying movement destination of the bed in a case where two or more sites are imaged.

FIG. 13, (a) shows a screen before input of the movement destination. On this screen, a mark 308 indicating center of opening (henceforth referred to as center of opening 308) is displayed at the center of the screen, and the movable region 304, of which starting point is the position of the center of opening, is displayed. The display of the center of opening 308 and the movable regions 304 is fixed. On the other hand, the reference image 301 can be scrolled right and left on the screen. On this screen, the user drags the reference image with a mouse or the like to scroll the reference image right and left to move it to the position shown in FIG. 13, (b) from the position shown in FIG. 13, (a), and dispose it so that an objective site of imaging locates at the center of opening 308. The control device 203 calculates moved distance of the bed 106 on the basis of the position of the moved reference image, and sets the movement destination. Further, the control device 203 displays a region for which the scanogram 301 is not obtained at the time of obtaining the scanogram 301 on the display 201 as a complementary region 309, as shown in FIG. 13, (b).

The control device 203 may move FOV 303 so that it follows the movement of the reference image, or may display FOV 303 at the original position so that it does not follow the movement of the reference image.

Hereafter, the case of using the axial image 301a as a reference image will be explained.

FIG. 13, (c) shows a screen before input of the movement destination. On this screen, the user drags the reference image with a mouse or the like to scroll the reference image right and left or up and down to move it to the position shown in FIG. 13, (d). The control device 203 calculates moved distance of the bed 106 on the basis of the position of the moved reference image, and sets the movement destination. Further, the control device 203 displays a region for which the scanogram 301 is not obtained at the time of obtaining the scanogram 301 on the display 201 as a complementary region 309, as shown in FIG. 13, (d).

In both cases, the distance of movement of the reference image may be inputted as a numerical value instead of dragging the reference image with a mouse or the like.

The control device 203 may store the image moved as shown in FIG. 13, (b) and (d) in the storage device 204 as another reference image. Comparison of the CT image 205 and the reference image is thereby made easier after completion of the imaging.

Explanation of the case of using the scanogram 301 for the sagittal direction as a reference image is omitted, since it can be easily analogized from the case of using the scanogram 301 for the coronal direction.

In the fourth embodiment, the size of the complementary region 309 displayed on the display 201 is the same as the moved distance of the bed 106. This makes the user possible to easily understand at which position within the opening 105 the subject should be placed at the time of the imaging, and easily imagine actual movement of the bed 106. Further, even if a partial region of FOV 303 protrudes from the reference image, the protruding region is also superimposed and displayed on the complementary region 309, and therefore it becomes easy to judge to which position the region of FOV 303 extends.

Fifth Embodiment

This embodiment is characterized in that the movement destination setting unit has a function of, when the imaging is performed for a plurality of sites, setting a single movement destination of the bed that enables imaging of the plurality of sites.

The fifth embodiment will be explained below with reference to FIG. 14. The same elements as those of the aforementioned embodiments are indicated with the same numerals, and explanations thereof are omitted. In particular, flow of the operations of the X-ray CT apparatus 1 is the same as that of the second embodiment.

When imaging is performed for a plurality of sites, the bed 106 may be transversely moved for imaging of every sites, but there is a case where time of transverse movement of the bed 106 is desired to be shortened as much as possible, for example, a case where investigation is hurried. Therefore, in the fifth embodiment, imaging of a plurality of sites is performed with the same position of the bed 106 for the transverse direction (position for the X direction) so that the bed 106 is transversely moved only at the time of imaging of the first site, and thereby the investigation time is shortened.

First, the method of inputting the unified transverse movement destination 302 of the bed 106 performed by a user is explained. Even when the same GUI as that of the aforementioned embodiment is used, if the user inputs the same transverse movement destination 302 of the bed 106 for every site, the transverse movement destination 302 of the bed 106 can be unified, but time and effort is required for the user to input the same transverse movement destination 302 of the bed 106 for every site. Therefore, there is provided GUI that enables setting of a single transverse movement destination 302 of the bed 106 in common with a plurality of sites.

Figure 14:
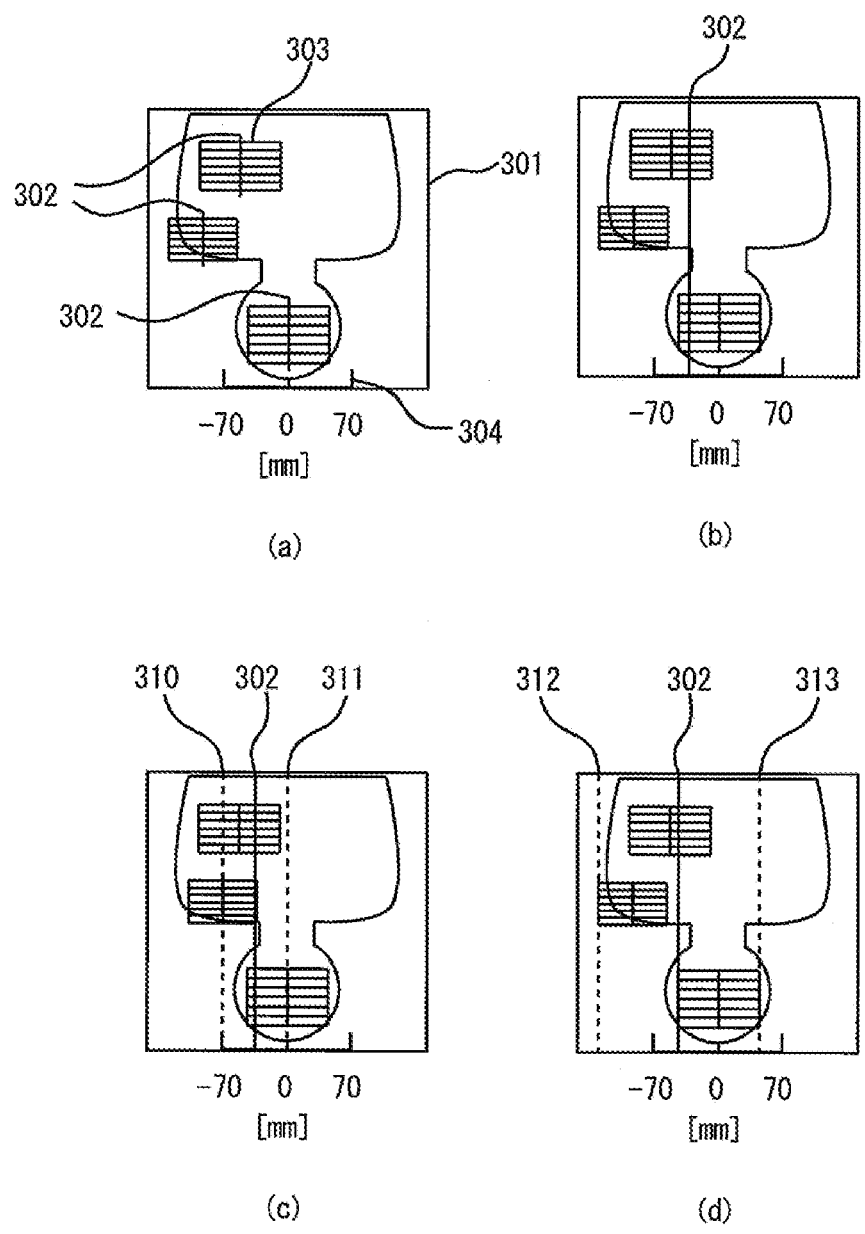

FIG. 14, (a) shows a state that the transverse movement destination 302 is set for each site. FIG. 14, (b) shows a state that the control device 203 can set a unified transverse movement destination, to which the state of FIG. 14, (a) is changed by a user through pushing a button for setting of unified transverse movement destination. The user sets the unified transverse movement destination 302 of the bed 106 by using GUI shown in FIG. 14, (b).

The method of setting the unified transverse movement destination 302 of the bed 106 performed by the control device 203 on the basis of a plurality of the transverse movement destinations 302 of the bed 106 inputted by the user will be explained below.

The user sets the transverse movement destination 302 of the bed 106 for every site as shown in FIG. 14, (a). The control device 203 determines, among the plurality of the transverse movement destinations 302 of the bed 106, the transverse movement destination 302 locating at the leftmost position to be the leftmost part 310 of the transverse movement destination, and the transverse movement destination 302 locating at the rightmost position to be the rightmost part 311 of the transverse movement destination, as shown in FIG. 14, (c). Then, the control device 203 sets, for example, the middle point of the leftmost part 310 of the transverse movement destination and the rightmost part 311 of the transverse movement destination as the unified transverse movement destination 302 of the bed 106.

Further, as another example, as shown in FIG. 14, (d), the control device 203 determines, among a plurality of FOVs 303 of the bed 106, the left end part of FOV 303 locating at the leftmost position to be the leftmost part 312 of FOV, and the right end part of FOV 303 locating at the rightmost position to be the rightmost part 313 of FOV. Then, the control device 203 sets, for example, the middle point of the leftmost part 312 of FOV and the rightmost part 313 of FOV as the unified transverse movement destination 302 of the bed 106.

When a plurality of sites are imaged, if a unified transverse movement destination 302 of the bed 106 is set, and the bed 106 is transversely moved only at the time of imaging of the first site as in the fifth embodiment, it becomes possible to attain both shortening of investigation time and reduction of dose.

The unified transverse movement destination 302 of the bed 106 is not limited to that for all the sites. For example, when the user selects a plurality of the transverse movement destinations 302 of the bed 106 for sites for which a unified transverse movement destination is desired, the control device 203 may set the unified transverse movement destination 302 of the bed 106 on the basis of the plurality of the selected transverse movement destinations of the bed 106.

Sixth Embodiment

This embodiment is characterized in that the display 201 has a function of displaying a site suffering large cumulative dose (cumulative dose warning region), in addition to the function of displaying the movement destination and movable region of the bed.

That is, in the sixth embodiment, the X-ray CT apparatus 1 sets the movement destination of the bed 106, while the user confirms a site suffering large cumulative dose (cumulative dose warning region 323) displayed together with the reference image. The sixth embodiment will be explained below with reference to FIG. 15. The same elements as those of the aforementioned embodiments are indicated with the same numerals, and explanations thereof are omitted. In particular, flow of the operations of the X-ray CT apparatus 1 is the same as that of the second embodiment.

Cumulative doses for every subject and every site are stored beforehand in the storage device 204.

Figure 15:
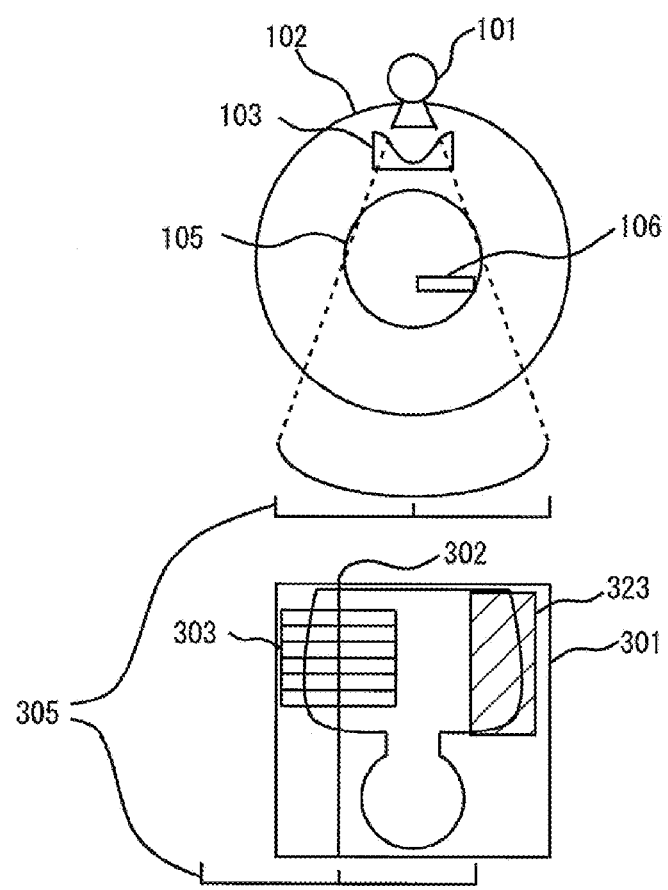
FIG. 15 shows an example of display of a cumulative dose warning region.

When the control device 203 displays the scanogram 301, it addresses the storage device 204 to obtain cumulative dose for each site of a corresponding subject. Then, the control device 203 judges whether the cumulative dose for each site exceeds a predetermined threshold value. And as shown in FIG. 15, the control device 203 superimposes a site of which cumulative dose exceeds the predetermined threshold value as a cumulative dose warning region 323 on the scanogram 301 and displays it on the display 201. In FIG. 15, cumulative dose of the subject's right arm is large, and therefore the transverse movement destination 302 of the bed 106 is shifted so that the subject's right arm should not in the imageable region 305.

According to the sixth embodiment, the user can input FOV 303 with confirming that an objective site of imaging is in the imageable region 305, and a site suffering large cumulative dose (cumulative dose warning region 323) is not in the imageable region 305.

In the sixth embodiment, the cumulative dose warning region 323 is stored in the storage device 204 and displayed on the display 201. However, instead, a function of calculating dose for each site on the basis of the bow tie filter 103 set in the control device 203 may be added, and a cumulative dose warning region 323 may be displayed on the display 201 on the basis of the cumulative dose obtained from the calculated dose.

Further, in the sixth embodiment, a site suffering large cumulative dose is displayed. However, instead, a region for which irradiation of X-rays is undesired (bones, reproductive organs, etc.) may be displayed. And the control device 203 may set the transverse movement destination and up and down movement destination of the bed 106 so that a region for which irradiation of X-rays is undesired is separated from the center of the opening 105 as much as possible.

Preferred embodiments of the X-ray CT apparatus etc. of the present invention were explained above with reference to the appended drawings. However, the present invention is not limited to these embodiments. For those skilled in the art, it is apparent that various alterations and modifications are possible according to the technical principles disclosed by this patent application, and it should be understood that they are of course fall within the technical scope of the present invention.

DESCRIPTION OF NUMERICAL NOTATIONS

1 . . . X-ray CT apparatus
100 . . . Scanning gantry part
101 . . . X-ray tube
102 . . . Gantry (revolving disk)
103 . . . Bow tie filter
104 . . . Collimator
105 . . . Opening
106 . . . Bed
107 . . . X-Ray detector
108 . . . Data acquisition device
109 . . . X ray control device
110 . . . Interlock control device
111 . . . Bed control device
112 . . . Gantry control device
120 . . . System control part
121 . . . System control device
122 . . . Image arithmetic unit
123 . . . Storage device
124 . . . Raw Data
2 . . . Console
201 . . . Console display
202 . . . Console input device
203 . . . Console control device
204 . . . Console storage device
205 . . . CT image
301 . . . Scanogram
302 . . . Transverse movement destination
303 . . . FOV (field of view, reconstruction region)
304 . . . Transversely movable region
305 . . . Imageable region
306 . . . Up and down movement destination
307 . . . Up and down movable region
308 . . . Center line of opening
309 . . . Complementary region
310 . . . Leftmost part of transverse movement destination
311 . . . Rightmost part of transverse movement destination
312 . . . Leftmost part of FOV
313 . . . Rightmost part of FOV
321 . . . Non-imageable region
322 . . . Center of FOV
323 . . . Cumulative dose warning region

What is claimed is:

1. An X-ray CT apparatus comprising:
a reference image acquisition unit that acquires a reference image by irradiating a subject placed on a bed with X-rays,
a movable region calculating unit that calculates a transversely movable region of the bed on the basis of height of the bed and size of the subject, and/or calculates an up and down movable region of the bed on the basis of position of the bed for the transverse direction and size of the subject,
a movement destination setting unit that sets a movement destination of the bed within the transversely movable region and/or the up and down movable region calculated by the movable region calculating unit,
a filter size setting unit that sets size of a filter for adjusting radiation intensity of the X-rays,
an imageable region calculating unit that calculates an imageable region on the basis of the movement destination of the bed set by the movement destination setting unit and the filter size set by the filter size setting unit, and
a displaying unit that displays the imageable region calculated by the imageable region calculating unit superimposed on the reference image.

2. The X-ray CT apparatus according to claim 1, wherein the displaying unit further displays the transversely movable region and/or the up and down movable region calculated by the movable region calculating unit superimposed on the reference image.

3. The X-ray CT apparatus according to claim 1, wherein the X-ray CT apparatus further comprises a tilt angle setting unit that sets a gantry tilt angle, and
the movable region calculating unit calculates the transversely movable region and/or the up and down movable region further on the basis of the tilt angle set by the tilt angle setting unit.

4. The X-ray CT apparatus according to claim 1, wherein when the transverse movement destination and/or the up and down movement destination of the bed displayed on the displaying unit is moved by a user, the movement destination setting unit calculates distance of movement of the bed on the basis of the moved transverse movement destination and/or up and down movement destination of the bed, and sets a movement destination of the bed.

5. The X-ray CT apparatus according to claim 1, wherein when the reference image displayed on the displaying unit is moved by a user, the movement destination setting unit calculates distance of movement of the bed on the basis of position of the moved reference image, and sets a movement destination of the bed.

6. The X-ray CT apparatus according to claim 5, wherein when the reference image displayed on the displaying unit is moved, the displaying unit identifiably displays a region not obtained at the time of imaging for obtaining the reference image.

7. The X-ray CT apparatus according to claim 1, wherein when imaging is performed for a plurality of sites, the movement destination setting unit sets a single movement destination of the bed for the plurality of sites on the basis of FOVs or movement destinations set for every site through an input device.

8. The X-ray CT apparatus according to claim 7, wherein the X-ray CT apparatus comprises a cumulative dose calculating unit that calculates cumulative dose for every site, and
the displaying unit displays a site suffering large cumulative dose as a cumulative dose warning region.

9. An X-ray CT apparatus comprising a gantry that has an opening and can be tilted with respect to the vertical direction, and a bed that can move in the opening of the gantry, which is provided with:
a reference image acquisition unit that collects a reference image by irradiating a subject placed on the bed with X-rays, a movable region calculating unit that calculates a movable region of the bed on the basis of positional information of the bed, tilt angle of the gantry, and size of the subject, a movement destination setting unit that sets a movement destination of the bed in the movable region calculated by the movable region calculating unit, and a displaying unit that displays the movable region of the bed and/or the movement destination of the bed set by the movement destination setting unit together with the reference image.

10. The X-ray CT apparatus according to claim 9, wherein:

the movable region calculating unit calculates a transversely movable region of the bed on the basis of the positional information of the bed for a direction of a height of the bed.

11. The X-ray CT apparatus according to claim 9, wherein:

the movable region calculating unit calculates an up and down movable region of the bed on the basis of the positional information of the bed for a horizontal direction perpendicular to a direction of a height of the bed.

12. The X-ray CT apparatus according to claim 9, wherein:

the X-ray CT apparatus further comprises a filter size setting unit that sets size of a filter for adjusting radiation intensity of the X-rays, and an imageable region calculating unit that calculates an imageable region on the basis of the movement destination of the bed set by the movement destination setting unit and the filter size set by the filter size setting unit, and the displaying unit displays the imageable region calculated by the imageable region calculating unit superimposed on the reference image.

13. The X-ray CT apparatus according to claim 9, wherein:

the displaying unit is provided with a GUI that receives setting of the movement destination of the bed and/or setting of FOV from a user.

\* \* \* \* \*